United States Patent [19]

Gilbert et al.

[11] Patent Number: 5,052,381
[45] Date of Patent: Oct. 1, 1991

[54] ADHESIVE WOUND DRESSING AND PERFORATED SHIELD

[75] Inventors: Eugene C. Gilbert, Brecksville; William N. Schenk, Peninsula, both of Ohio

[73] Assignee: The B.F. Goodrich Company, Brecksville, Ohio

[21] Appl. No.: 495,664

[22] Filed: Mar. 19, 1990

[51] Int. Cl.$^5$ .................... A61F 13/00; A61F 15/00; A61L 15/00
[52] U.S. Cl. .................................. 128/155; 206/441
[58] Field of Search ............... 128/155, 887, 888, 893, 128/894, DIG. 20; 206/440, 441; 604/304, 307

[56] References Cited

U.S. PATENT DOCUMENTS

| 3,018,881 | 1/1962 | Wall | 206/56 |
| 4,413,621 | 11/1983 | McCracken et al. | 128/156 |
| 4,513,739 | 4/1985 | Johns | 128/156 |
| 4,614,183 | 9/1986 | McCracken et al. | 128/156 |
| 4,708,613 | 2/1989 | Koehnke et al. | 128/155 |
| 4,787,380 | 11/1988 | Scott | 128/156 |
| 4,815,457 | 3/1989 | Mazars et al. | 128/155 |

FOREIGN PATENT DOCUMENTS

| 8699 | of 1895 | United Kingdom | 604/304 |
| 842617 | 7/1960 | United Kingdom | 128/155 |

Primary Examiner—Randy Citrin Shay
Assistant Examiner—Paul Prebilic
Attorney, Agent, or Firm—Alfred D. Lobo; Nestor W. Shust

[57] ABSTRACT

A simple construction of a two-component adhesive film, external wound dressing, comprises a backing sheet of thin, preferably elastomeric and water vapor-permeable film protected by a release layer comprising two release sheets. The sheets not only protect the adhesive coating on the front face of the film, but also are instrumental in allowing the film to be precisely positioned over a wound, then gradually tensioned with a force no greater than the peel strength for the release sheets, while the dressing is applied. This feature of the dressing allows it to be smoothly applied over the wound with a predetermined amount of force while conforming the film to the contours of an injured body. This features is the result of providing each first and second release sheets with a relatively wide margin, at least 1.25 cm (0.5 inch) wide. The peel strength for each release sheet is essentially identical. In a first embodiment of the dressing, the first release sheet has a first side-margin defined by a fold line running laterally across the longitudinal axis; and the second release sheet has a second side-margin defined by an interrupting line of spaced apart incisions, slits or perforations. In the second embodiment of the dressing each of the release sheets has a side-margin defined by an interrupting line. In either embodiment, no greater force is required to peel each release sheet on either side of the fold line or interrupting line which defines a margin. Another embodiment of the dressing is an "island dressing" in which a pad of fabric has deposited in it, a layer of hydrophilic absorbent polymer to provide an absorptive dressing. The front surface of the pad may be coated with adhesive to facilitate application of the dressing, or be left uncoated.

27 Claims, 5 Drawing Sheets

ADHESIVE WOUND DRESSING AND PERFORATED SHIELD

BACKGROUND OF THE INVENTION

Over the entire history of man, the treatment of wounds has occupied pre-eminent importance for obvious reasons, yet remarkably little is understood about the mechanics of healing a wound. Many centuries after the recorded history of medicine was first begun, wound dressings still in use have run the gamut of materials and medicaments including synthetic and natural fibers for pads and bandages, and poultices of leaves, crushed seeds, clays and muds of various types, etc. and mixtures of the foregoing. It is only in the very recent past that any significant effort has been devoted to how best select a wound dressing for a particular wound. It is only still more recently that, galvanized by the need for efficient and speedy patient-care demanded by present day health care organizations, much attention has been devoted how better to deliver a wound dressing quickly, effectively and aseptically to the wound site, than a conventional adhesive wound dressing. These efforts have evolved into the use of "adhesive film wound dressings", which are constructed for a particular application and are appropriately sized so as to permit the use of the dressings on a relatively large area of human skin.

By the term "adhesive film wound dressing" we refer to one comprising a laminar backing sheet or strip of oxygen-permeable and water vapor-permeable synthetic resinous thin film, less than 2 mils thick, which is coated over at least a portion of one surface with a biocompatible, pressure-sensitive adhesive for directly adhering the dressing over a wound surrounded by skin. Such wound dressings necessarily provide a barrier against infectious microorganisms and are typically essentially impervious to liquid water and wound exudate which is confined by the dressing when it is adhesively secured over a wound.

An adhesive film wound dressing may include on its adhesive-coated side, an absorbent pad of porous material to be placed around, or in contact with the wound. Such pad-including dressings are referred to as "island dressings". All reference to a "wound dressing" or "dressing" refers to an adhesive film wound dressing which may also be an island dresing. A dressing without an island is referred to as a "film only" dressing.

The proportion of the surface of the film coated with adhesive is not narrowly critical, but the wound dressing of this invention is of the type in which the adhesive coats the major portion of the area to be placed in contact with the skin, and more preferably, substantially the entire surface of the dressing to be in contact with the skin.

Since the adhesive is pre-applied to the dressing, the coated surface must be protected while the dressing is packaged, shipped and sorted prior to being used. Just prior to applying the dressing, the protection must be removed and the dressing applied aseptically to the wound without letting the adhesive surface of the dressing stick to any other surface (including the fingers of the hands applying the dressing) than over the wound area.

Smoothly applying the adhesive dressing over the wound, without wrinking the dressing, and with a minimum of fuss and bother, is of crucial importance if the dressing is to gain acceptance among persons expected most frequently to apply it, namely those in the health care field, such as nurses and physicians.

Numerous dressings have been disclosed which purport to satisfy the foregoing criteria but have fallen short of their promise for one reason or another. A recent, commercially available dressing is disclosed in U.S. Pat. No. 4,513,739 to Johns (class 128/subclass 156) and has met with qualified success; a less recent one is disclosed in U.S. Pat. No. 3,018,881 (class 206/subclass 441). Both emphasize the need to provide an easy delivery system for delivering the adhesively-coated film to the wound site; and each focuses the critical importance of removing the release sheets, which provide a protective shield, in such a way as to make positioning the dressing on the wound a simple and expeditious task.

It is self-evident that the dressing must be placed over the wound without having one portion of the adhesive surface contact another, because the adhered portions cannot generally thereafter be separated. It is also self-evident that the release sheets cannot be pulled off the adhesive surface, in toto, before the dressing is placed over the wound, because one would then have lost manual control of the dressing, and if such control was retained, the dressing could not be applied aseptically. Therefore, it is essential that the release sheets on the adhesively coated film be so constructed that they not only provide aseptic protection for the coated front surface of the film, but also that, when pulled upon, they do not come off in toto, but only partially, thus providing the nurse, or other person, a chance to position and adhere the dressing precisely where it is to be located over the wound.

To this end, the '739 and '881 references each introduces an element which provides such a chance in the form of a release-retarding means along one edge or a pair of opposed edges of the dressing, so that a greater force is required to separate the release sheet at the edge than that required to separate the sheet from the remainder of the contacting area. The '881 patent simply discloses that flap 32 and panel 14 of the bandage are peelably or strippably adhered to the ends of portions 26 and 28 respectively, but the '739 patent specifies numerous release-retarding means for providing the greater peel strength at the edges of the dressing.

Among the release-retarding means suggested in the '739 patent are (1) a strip of flexible tape attached to the second or rear face of the backing sheet to provide a heat sink for an infra-red heat source used to increase the adhesive strength at the edges; (2) a strip of backing sheet having a thickness greater than that of the remainder of the backing sheet; (3) a strip of adhesive on the front face of the backing sheet to provide greater tenacity than the biocompatible adhesive covering the rest of the sheet; inter alia.

The extreme simplicity of the design and construction of the basic embodiments of our wound dressing requires the use of only two components, namely the adhesively coated film, and a release layer comprising two release sheets. An additional element, namely an absorbent pad may be included, if an island dressing is desired. The simple design eschews the introduction of release-retarding means suggested by the prior art, yet provides an equivalent function in the form of a interrupting line of incisions or perforations which provide a "temporary stop" in only one, or both release sheets in first and second embodiments respectively, during the removal of the sheets, prior to application of the dressing. The temporary stop is provided without introducing an additional structural element. We simply provide the interrupting line of incisions or perforations pierced through at least one release sheet, the piercing being effected in a direction from the outer surface of the release sheet to its inner surface which is in contact with the adhesive surface of the film, referred to as the "front" surface.

Moreover, we have found that the location of the "temporary stop" as it is provided in our release sheet(s) at least 1.25 cm from a side-edge, is critical if the dressing is to be applied with slight pressure in a direction normal to the surface of the skin of a patient in the supine position, the pressure being exerted downwardly upon the wound, simultaneously with a pulling action which provides tension in a lateral plane. Locations suggested by the '739 and '881 references, of their release-retarding means along one or both edges of their films, simply fail to provide the necessary distribution of tensile forces over the surface area of the dressing, for smoothly tensioning the dressing during the final stages of the application procedure. The temporary stop provided by the interrupting line of incisions or perforations in spaced-apart relation from the edges of the film, so as to provide relatively wide, opposed side-margins to distribute tensile forces over the film, allows one to do so.

SUMMARY OF THE INVENTION

It has been discovered that an extremely simple construction of a two-component adhesive film, external wound dressing comprising a backing sheet of thin, preferably elastomeric film, protected by a release layer comprising two release sheets which are removed by pulling them off in opposite directions, provides an unexpectedly effective delivery system for smoothly and expeditiously applying the wound dressing aseptically over the wound in an injured body.

It is therefore a general object, in a first embodiment of this invention, to provide a two-component wound dressing of arbitrary over-all shape and size, comprising, an elastomeric film uniformly coated over at least some portion, and preferably a major portion of its wound-contacting or "front" surface, with a biocompatible adhesive, the film having opposed first and second side-margins wide enough in relation to the area of the dressing to permit the film to be tensioned while it is being applied; and a release layer comprising first and second release sheets which together completely cover the adhesive, the area of the front surface covered by one sheet being larger (hence referred to as the 'larger sheet') than that covered by the other (which is referred to as the 'smaller sheet'). Each release sheet is cut from the same stock and becomes adhesively secured to the wound-contacting front surface to the same degree as the other so that the peel strength (oz/inch of width) measured over any portion of uninterrupted area of release sheet in contact with adhesive, is identical. One end of the smaller sheet is folded upon itself, and a folded portion adhered to the first side-margin of the film, so the non-adhered folded portion serves as a gripping tab. The larger sheet is provided with an interrupting line of incisions, slits or perforations, this line being at right angle to the longitudinal direction in which the release sheets are to be pulled when they are removed. The larger sheet is adhered to the remaining portion of adhesive not covered by the smaller sheet, the non-adhered end portion of the large sheet overlying the smaller sheet, so that no portion of the adhesive is left uncovered.

It is a specific object of this invention to provide the foregoing first embodiment of the invention with an absorbent pad adhesively secured to the adhesive coated face of the film, the pad being positioned intermediate the opposed side margins, preferably symmetrically disposed about the lateral centerline of the dressing. The pad absorbs exudate from the wound and may be coated or impregnated with medicaments to facilitate or accelerate wound healing, or to improve absorption of exudate.

It is also a general object, in a second embodiment of this invention, to provide a two-component wound dressing comprising the foregoing adhesively coated, thin elastomeric film having first and second side-margins and release sheets which together completely cover the adhesive. The first and second release sheets are each provided with first and second interrupting lines, respectively, of spaced-apart interruptions made as herebefore, to define first and second side-margins each at least 1.25 cm wide. The second release sheet overlies the first which is long enough to extend to about the lateral center-line of the dressing, the end of the first sheet being folded exteriorly upon itself to provide a first gripping tab.

It is another general object, in a modification of the second embodiment of this invention, to provide the second embodiment described immediately hereinabove with side-margins equidistantly spaced apart from the lateral center line, and a pair of release sheets having essentially the same area and a common fold line for their respective folded-over ends which provide gripping tabs. The symmetrical design provides better manual control of the dressing and more uniform application over a wound.

It is also a specific object of this invention to provide a body-conformable elastomeric polyurethane thin film, preferably about 1 mil thick, as the backing sheet of a wound dressing, the film being uniformly coated over its entire surface with a biocompatible water-vapor permeable adhesive, which in addition, may be porous. The adhesive surface is protected with a pair of silicone release-coated paper sheets, one larger in area than the other, both sheets adhesively secured near their longitudinally opposed side-end portions, to opposed side-margins of the film in such a manner that the act of pulling apart the release sheets by pulling on gripping tabs provided by the release sheets, facilely exposes the adhesive front surface of the film and allows it to be deftly positioned aseptically upon the wound as a natural consequence of the act.

It is also a specific object of this invention to provide the foregoing second embodiment of the invention with an absorbent pad, to form an "island dressing" in a manner analogous to that described hereinabove for the first embodiment.

BRIEF DESCRIPTION OF THE DRAWING

The foregoing and other objects and advantages of our invention will appear more fully from the following detailed description, made in connection with the accompanying drawings of preferred embodiments of the invention the components of which are not to scale and greatly exaggerated for purposes of illustration, and wherein like reference characters refer to the same or similar parts throughout the views and in which:

FIG. 3 is a side elevational view of the wound dressing of FIG. 1, in its normal pre-application position, namely adhesive coating down, in which the position of the fingers holding one (the first) side-margin, preferably about 1.25 cm wide for normal human use) on the first release sheet, is schematically illustrated while only the second release sheet, which is larger in area than the the first, is temporarily "stopped" during the process of applying the wound dressing, at a line of interrupting incisions, the line being at least 1.25 cm (0.5 inch) from the edge of the backing sheet (film); the first release sheet has not as yet begun to be stripped. The first release sheet is held in place by the index and middle fingers gripping the gripping tab, the opposed portion of the dressing being held at the first side-margin between the thumb and index finger. In the position illustrated, the dressing is supported and allows the use of an equal and opposite resistance force to counter that exerted by the pulling action of the second (larger) sheet:

DETAILED DESCRIPTION OF PREFERRED EMBODIMENTS

In the first embodiment, a "film only" external wound dressing (so termed to distinguish it from an "island" external wound dressing) is schematically illustrated as a rectangular dressing, in FIGS. 1-4, though the shape and size are arbitrary. This wound dressing is indicated generally by reference numeral 10 in FIG. 1 which shows a top plan view in which the bottommost layer is a biocompatible adhesive 11 uniformly coating the entire front face of a continuous or microporous elastomeric film 12. The film and adhesive coating are each typically less than about 2 mils thick, the latter being protected with flexible first and second release sheets 13 and 14 respectively, each strippably adhered to first and second portions of the adhesive coating, commencing from opposed side-margins m' and m' respectively, of the adhesive-coated rectangle. The release sheets are typically less than 5 mils thick and cut from the same stock so that the peel strength, which is a measure of the degree of adhesion of each unit area of sheet stock to adhesive, is the same for each sheet. Thus the force required to peel each release sheet from the adhesive is the same. Release sheet 13 is folded upon itself along fold-line 15 which is paralled to, and spaced-apart (by the width of the margin m') from the outer side-edge of the sheet, so that the sheet's inner end (that is, the end opposite from the outer end lying along the outside edge of the rectangle) provides a gripping tab 13' which overlies the exterior surface of the release sheet 13. The extent to which tab 13' overlies the portion 13 adhesively secured at margin m', is not narrowly critical provided it affords purchase for the thumb and index finger of a hand. Thus, the tab 13' may extend to the side-edge of sheet 13 or beyond, but there is no reason to provide a larger tab 13' than can be conveniently gripped between the index and middle fingers.

Figure 1:
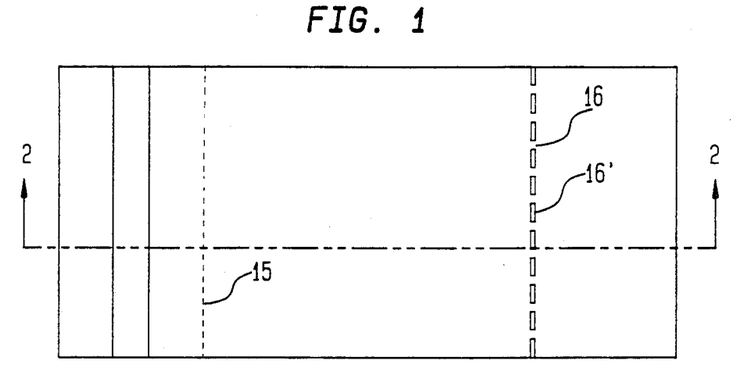
FIG. 1 is a top plan view with the release sheets on top and the film on the bottom, of a first embodiment of the wound dressing according to the present invention.
Figure 2:
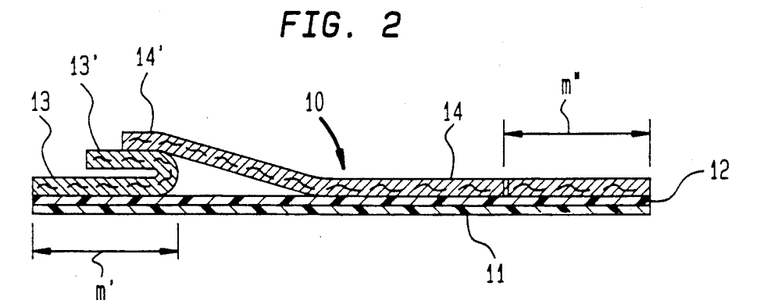
FIG. 2 is a cross-sectional view of the wound dressing of FIG. 1, taken along the line 2—2.

The portion of the adhesive coating not covered by the folded release sheet 13 is covered by the second release sheet 14 which is in contact with the adhesive and strippably adhered thereto. The inner end of the second release sheet provides a gripping tab 14' which overlies the upper surface of the folded-over gripping tab 13'.

In spaced-apart relation and paralled to the outer side-edge of release sheet 14 is a line 16 of interruptions 16', which may be incisions, slits or perforations. This line 16 is drawn through the center-line of the interruptions and runs laterally across, in a direction perpendicular to the longitudinal axis of the dressing. It is referred to as an "interrupting line" because it not only connects a multiplicity of linearly disposed interruptions in end-to-end spaced-apart relation, but it is the line at which stripping of the release sheet 14 is temporarily stopped. Incisions are made having a length in the range from about 0.1 mm to about 12 mm, preferably from about 1 mm to 5 mm with an instrument having multiple sharp knife-edges linearly spaced apart, one from the other, by less than about 5 mm, and the incisions have essentially no width. Slits or perforations are typically less than 5 mm in any dimension with an average area generally less than about 25 m$^2$, and are spaced apart like the incisions.

When incisions are made, there is no discernible removal of stock from the release sheet, but if the sheet is slitted or perforated, it will be evident that stock must be removed. Whether incisions are made, or the sheet is perforated, the sheet is pierced in the downward (in this top plan view) direction, that is, in the direction of the adhesive coating.

The line 16 defines a second side-margin m" which must be wide enough to transmit a tensioning force exerted uniformly over the length of the margin thus allowing a gradual tensioning of the film to conform it and smooth it onto the skin while the dressing is being applied. The width of the side margin m' is determined by the configuration of human fingers since the margin must provide sufficient space to afford a grip between the index and middle fingers of one hand. Since the length of a wound dressing of this invention is typically at least 7.5 cm in the longitudinal direction, that is from one side-edge to the other, it has been found that the margins m' and m" do not provide sufficient room for support and purchase of the digits of the hands of a typical adult human, to tension the dressing while it is being placed in contact over the wound, unless each side-margin is at least 1.25 cm in width.

Figure 8:
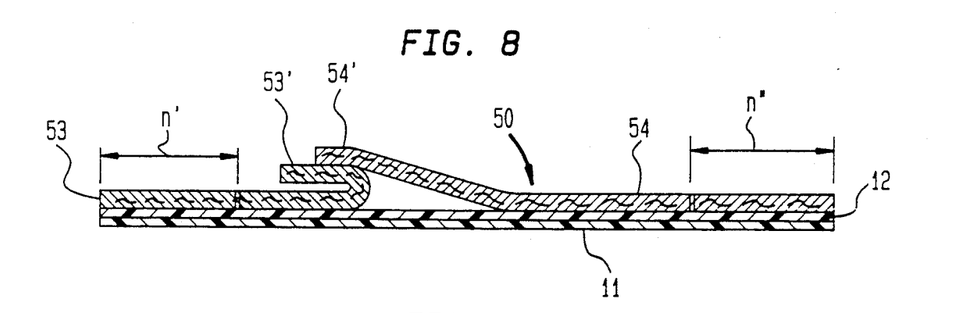
FIG. 8 is a cross-sectional view of the wound dressing of FIG. 7, taken along the line 8—8.

The position of the three components of the dressing are better seen in the cross-sectional view shown in FIG. 8 which is greatly enlarged and not to scale.

Figure 3:
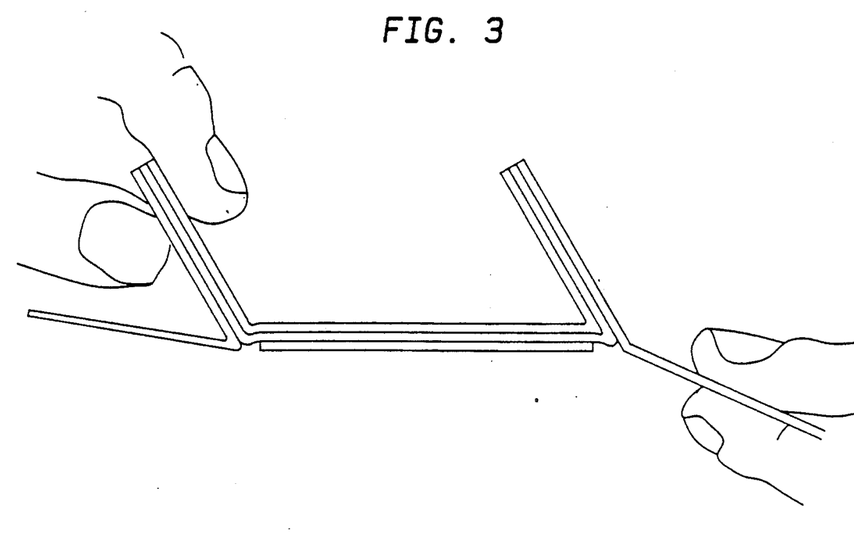
Figure 4:
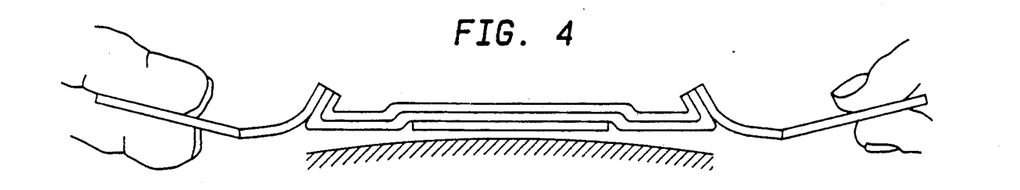
FIG. 4 is a side elevational view schematically depicting the position of the dressing over the wound, illustrating how the relative positions of the release sheets is changed from the temporarily stopped position of FIG. 3, while the dressing is being tensioned after it is positioned over the wound; no further illustration of the relative position of the release sheets is illustrated because further pulling on the sheets results in their being stripped entirely from the film.

As seen in FIG. 3, sufficient support for the dressing is provided just before it is applied, by simply stripping only the second release sheet 14, using just enough force to do so as is dictated by the peel strength of the adhesive bond between the release sheet and the adhesive. The peeling sheet stops at the interrupting line affording time to position the dressing exactly where it is to be placed. After the dressing is positioned in contact with the wound, the thumb under the margin m' may be withdrawn so that the gripping tab 13 is held only between the middle and index fingers, and peeling of both sheets is continued using the same force as was required to strip the release sheet 14 to the interrupting line. As seen in FIG. 4, tension on the film 12 is applied immediately after the dressing is positioned in contact with the skin, and this tension is maintained while each release sheet is being stripped the remaining distance to the respective opposed side-edges. The adhesive and release sheet stock are so chosen as to provide the desired tensioning for smoothly applying the dressing over a wound.

Figure 5:
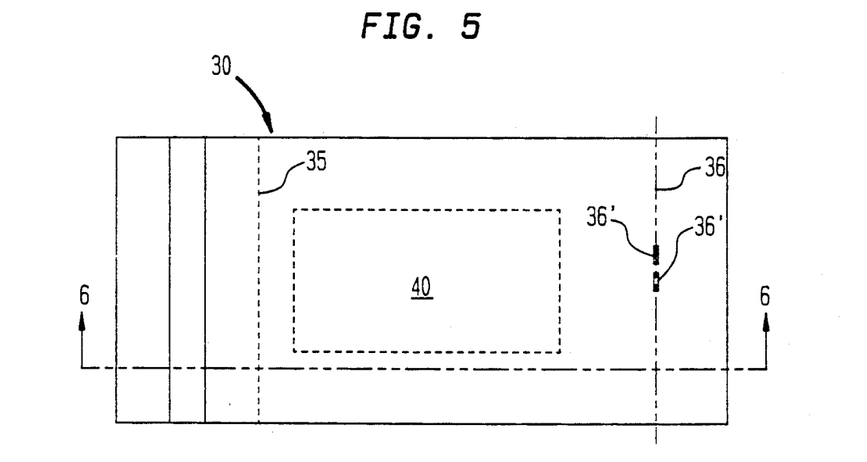
FIG. 5 is a top plan view of an "island" wound dressing in which an absorbent pad is adhesively secured intermediate opposed end margins of the film in the first embodiment; the "island" absorbent pad may include a medicament to facilitate healing of the wound, and/or a layer of hydrophilic material to increase absorption of exudate.

Referring now to FIG. 5 there is shown a plan view of an "island" dressing referred to generally by reference numeral 30, which has a construction analogous to that of the dressing 10 in FIG. 1, except that the island dressing is provided with an absorbent pad indicated generally by reference numeral 40 located intermediate the borders of the dressing, preferably near its geometrical center. As before, the dressing 30 comprises a film 12 coated with adhesive 11 and provided with first and second release sheets 33 and 34 respectively, the former being folded upon itself to provide gripping tab 33', and the latter having a row of incisions or slits 36' along an interrupting line 36 which provides a margin m" for the sheet 34. Fold-line 35 provides a margin m' for the side-margin of sheet 33, and the inner end 34' of sheet 34 overlies the gripping tab 33' to provide a gripping tab.

The pad 40 preferably comprises a gas-permeable fabric having desirable thickness 't' and upper and lower surfaces 41 and 42 respectively (FIG. 6), the pad formed from woven or non-woven fibers held in place by interlocking and frictional engagement with each other. For a typical rectangular island dressing the thickness t may be in the range from about 1 mm to about 2.5 cm or even more, though there is generally no significant benefit to be gained from thicknesses greater than 2.5 cm. Preferably fibers for the fabric are of cotton, polyesters, nylon or rayon, and the fabric is plural layers of surgical cellulose crepe tissue adhesively secured to the front face of the film 12. The pad may also be formed from one or more layers of woven fabric, such as woven cotton, the layers held in frictional engagement, one with the other.

Figure 6:
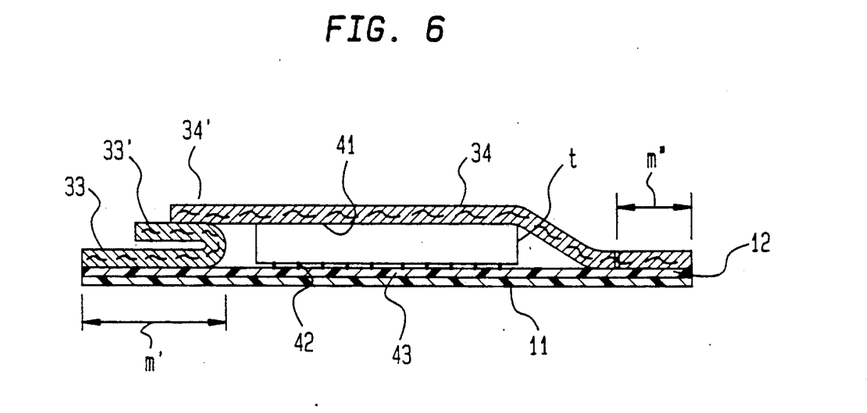
FIG. 6 is a cross-sectional view of the island wound dressing of FIG. 5, taken along the line 6—6.

If desired, for additional absorptivity, the lower or front face of the pad may have deopsited in the fibers, a layer 43 of non-toxic flexible hydrophilic material, preferably a crosslinked acrylic acid polymer in which a major proportion of the carboxylic acid groups are neutralized, as described in greater detail in Ser. No. 089,204 filed Aug. 25, 1987 the disclosure of which is incorporated by reference thereto as if fully set forth herein. As an alternative, the hydrophilic layer may be disposed intermediate the upper 41 and lower 42 faces of the pad. Though it will be evident that the function of absorbing exudate will be adequately met if the layer 43 is transversely disposed relative to the upper and lower surfaces, the layer is preferably generally parallel, being formed by simply dipping the front surface of fabric in the solution of monomer(s) which is then polymerized in situ. The thickness of the hydrophilic layer is not narrowly critical being determined by the size of the wound dressing in which it is used and the amount of exudate the dressing is expected to absorb. For small wound dressings the thickness may be as little as 5 mils, while for larger dressings expected to absorb a large amount of exudate, the thickness may be in the range as high as from about 3 mm to about 12 mm. The front face of the pad may be coated with the same or different adhesive as that coating the film, and typically is coated with the same adhesive, whether the pad is provided with a hydrophilic layer or not.

As will now be evident from the foregoing description and illustrations, to apply either the "film only" or "island" dressing of the first embodiment, a person must remove it from its standard sterile package, and with the release sheets facing the wound, grasp the gripping tabs. The gripping tab of the first (smaller) release sheet is grasped between the index finger and middle finger of one hand, the middle finger being nearest the wound, and the first side-margin of the first release sheet gripped between the index finger and thumb, the thumb being uppermost. The gripping tab of the larger sheet is gripped between the index finger and thumb of the other hand, the thumb being uppermost, and the two tabs pulled away from one another. The dressing is placed over the wound with the second (larger) release sheet peeled back to the interrupting line, and the second (smaller) release sheet not peeled away at all, so that the dressing is only partially applied over the skin surrounding the wound. The thumb of the hand gripping the first sheet is then removed and the two release sheets are removed in toto while the margins of the thin film are smoothly conformed to the skin over the contours of the body.

Figure 7:
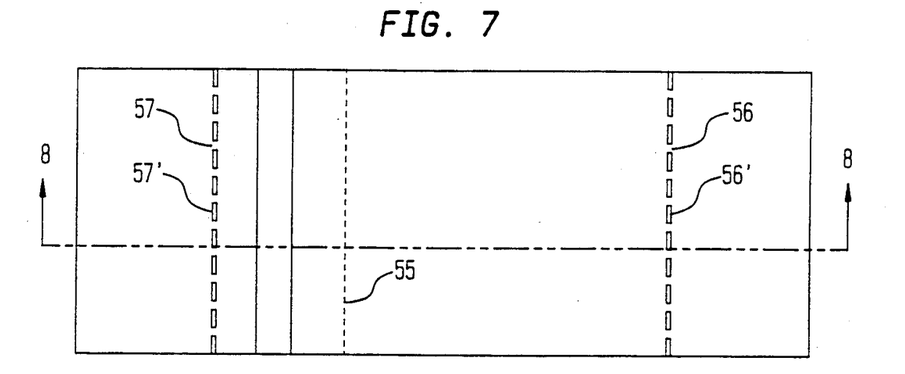
FIG. 7 is a top plan view with the release sheets on top and the film on the bottom, of a second embodiment of the wound dressing having an interrupting line in each of two release sheets, one sheet larger in area than the other.

In another embodiment schematically illustrated in FIGS. 7-10, a rectangular wound dressing indicated generally by reference numeral 50 in FIG. 7 is shown in a top view in which the bottommost layer is the biocompatible adhesive 11 which, as in the first embodiment hereinbefore, is uniformly coated over the entire front face of the elastomeric film 12. The adhesive coating is protected with first and second release sheets 53 and 54 (FIGS. 7-8) respectively, in a manner analogous to that described hereinabove, each commencing from opposed side-margins n' and n" respectively, and extending longitudinally, interiorly towards the center of the adhesive-coated rectangle. As before, each unit area of each release sheet has the same numerically quantifiable attachment to the adhesive coating, which attachment is measured by the peel strength of the sheets, which strengths are the same. Release sheet 53 is folded upon itself along fold-line 55 which is parallel to, and spaced-apart from the outside side-edge of sheet 53, so that the folded-over portion provides a gripping tab 53' overlying the outer surface of sheet 23.

The portion of the adhesive coating not covered by the folded release sheet 53 is covered by the second release sheet 54 which is in contact with the adhesive and strippably adhered thereto. The inner end of the second release sheet provides a gripping tab 54' which overlies the upper surface of the folded-over gripping tab 53'. In spaced-apart relation and paralled to the outer edge of release sheet 54 is a first interrupting line 56 of interruptions, whether incisions or perforations 56', as described hereinabove. The line 56 defines a second side-margin n" which, as before, must be wide enough, at least 1.25 cm wide, to allow a gradual tensioning of the film when the sheet is stripped past the interrupting line. The sheet 53 is also provided with a second interrupting line 57 of interruptions 57' spaced apart (by the width of the margin m') from and parallel to the outside side-edge of the sheet 53.

The position of the components of the dressing are better seen in the cross-sectional view shown in FIG. 8 which is greatly enlarged and not to scale. As will be evident, the area of the front surface covered by one (the second) release sheet is greater than that covered by the other (the first) because the fold-line 55 does not cross the lateral center line of the dressing. However, it will also be evident that if the fold-line crossed the center line, the relative areas of the front surface covered by each sheet would be reversed. Thus, the area covered by each sheet is not narrowly critical provided the fold line does not extend past the interrupting line 56.

The width of the side-margin n' is determined by the same considerations which determine the width of margin m'. Though illustrated as being of the same width, though, the side-margins may be of different widths, though, typically there is no compelling reason for using side-margins of differing widths.

Figure 9:
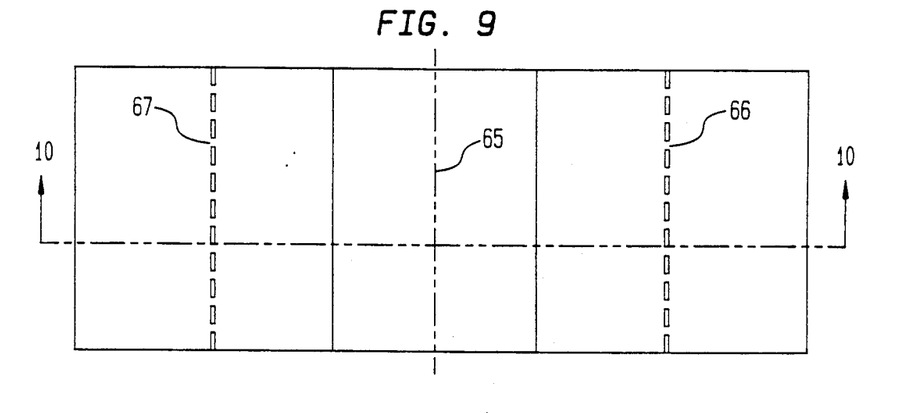
FIG. 9 is a top plan view with the release sheets on top and the film on the bottom, of another embodiment of the wound dressing having an interrupting line in each of two release sheets, each substantially equal in area to the other.
Figure 10:
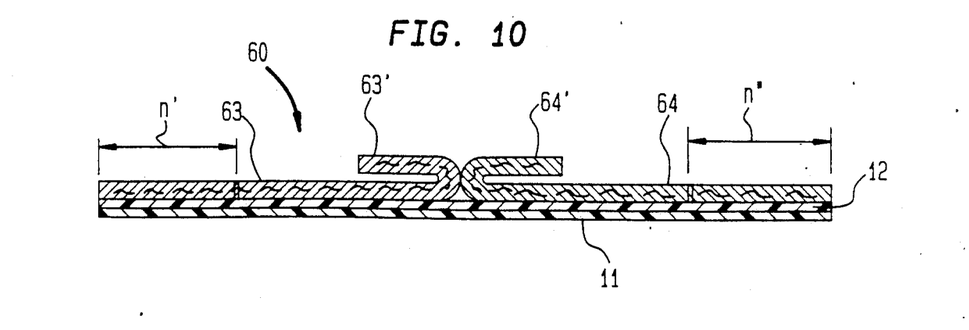
FIG. 10 is a cross-sectional view of the wound dressing of FIG. 9, taken along the line 9—9.

FIGS. 9-10 depict wound dressing 60 as a modification of the second embodiment illustrated in FIGS. 7-8. In this modification, the release sheets 63 and 64 provided with interrupting lines 66 and 67, and having folded-over end portions 63' and 64' respectively to provide gripping tabs, are symmetrically disposed about the center line so that the fold-lines of each sheet overlap because the ends abut each other, that is, the release sheets share a common fold-line 65. Thus each sheet covers one-half the area of the front surface, and the side-margins of essentially the same width are equidistant from the lateral center line.

It will now be evident that the construction of the foregoing embodiment with equidistant interrupting lines is designed to provide symmetrical longitudinal tension and downward pressure on the film as it is applied to the wound. This result is also obtained with release sheets which cover non-equal areas of the front face whether their fold-lines are in abutting or overlapping relationship.

Figure 11:
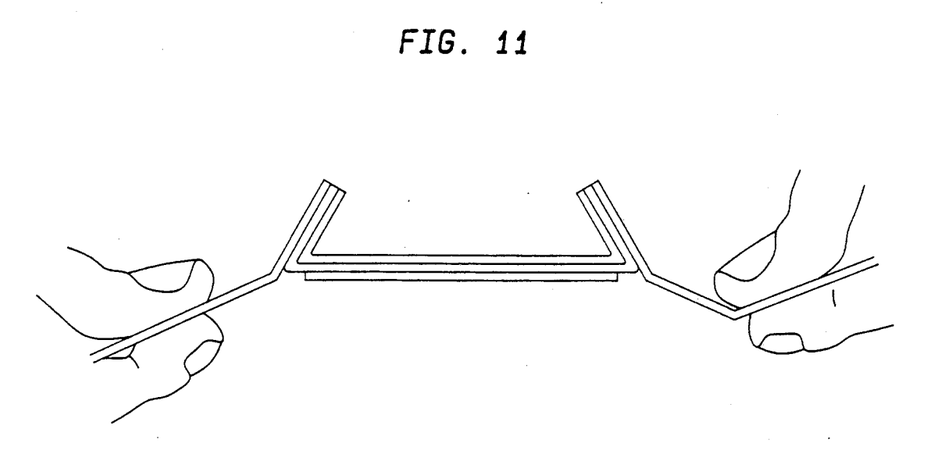
FIG. 11 is a side elevational view of the wound dressing of FIG. 9, in its normal pre-application position, namely adhesive coating down, in which is schematically illustrated the position of the thumb and index finger of one hand holding the gripping tab on the first release sheet, and the thumb and index finger of the other hand gripping the tab on the second release sheet; each release sheet is temporarily "stopped" at its line of interrupting incisions, each line being about 2.5 cm (1 inch) from the respective side-edges of the film. In the position illustrated, the dressing is supported and, as in the first embodiment, allows the use of an equal and opposite resistance force to counter that exerted by the pulling action on each of the release sheets.

As seen in FIG. 11, which illustrates the pre-application position of the dressing 60, sufficient support for the dressing is provided just before it is applied, by simply stripping both release sheets 63 and 64, using only the thumb and index finger of each hand and just enough force to allow the peeling sheets to stop temporarily at their respective interrupting lines, affording time to position the dressing exactly where it is to contact the wound. After the dressing is positioned in contact with the wound, peeling of both sheets is continued using the same force to strip each release sheet to its respective interrupting line.

Figure 12:
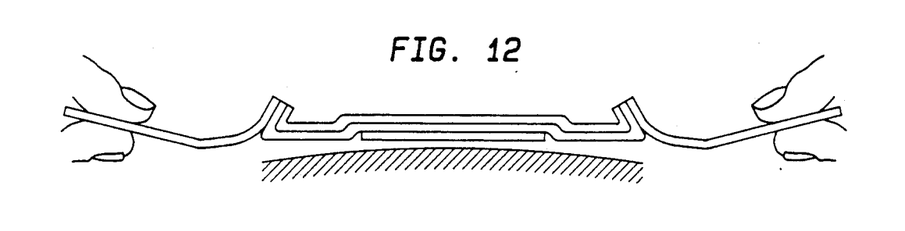
FIG. 12 is a side elevational view schematically depicting the position of the dressing over the wound, illustrating how the relative positions of the release sheets is changed from the temporarily stopped position of FIG. 11, while the dressing is being tensioned after it is positioned over the wound; no further illustration of the relative position of the release sheets is illustrated because further pulling on the sheets results in their being stripped entirely from the film.

As seen in FIG. 12, when tension on the film 12 is applied immediately after the dressing 60 is positioned in contact with the skin, and this tension is maintained, the release sheets are stripped the remaining distance to their respective opposed side-edges.

Figure 13:
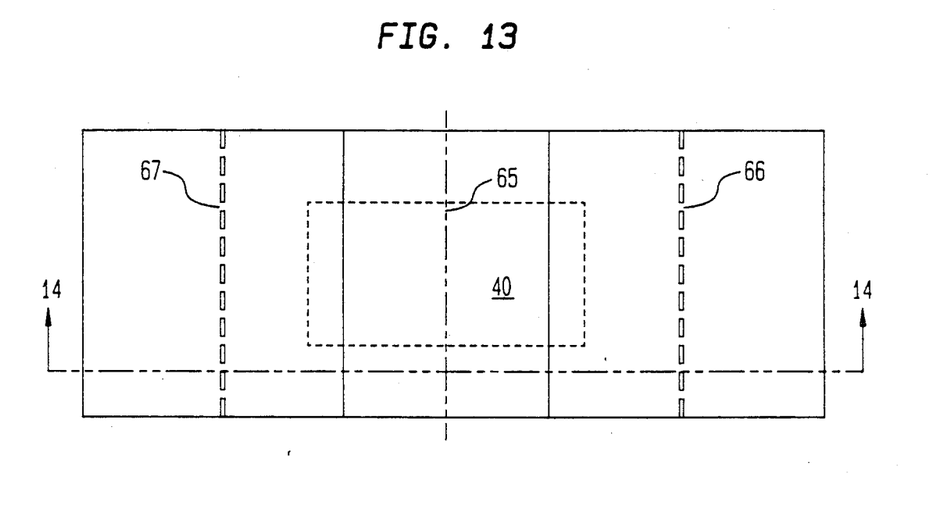
FIG. 13 is a top plan view of an "island" wound dressing in which an absorbent pad is adhesively secured intermediate opposed end margins of the film in the second embodiment illustrated in FIG. 9.
Figure 14:
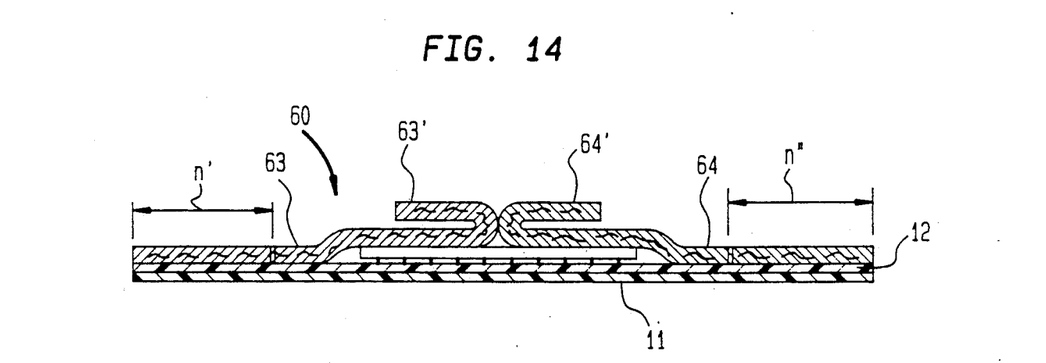
FIG. 14 is a cross-sectional view of the island wound dressing of FIG. 13, taken along the line 13—13.

Referring now to FIG. 13 there is shown a plan view of an "island" dressing modification of the second embodiment illustrated in FIGS. 9-10. This island dressing referred to generally by reference numeral 70, has a construction analogous to that of the dressing 60 in FIGS. 9-10 except that it is provided by absorbent pad 71 located centrally upon the adhesive-coated front face 11.

As will now be evident from the foregoing description and illustrations, to apply either the "film only" or "island" dressing of this second embodiment, a person must remove it from its standard sterile package, and with the release sheets facing the wound, grasp the gripping tabs of each sheet between the thumb and index finger of each hand, the thumbs being in opposed positions relative to each other, and the two tabs pulled away from one another. The dressing is placed over the wound with each release sheet peeled back to its respective interrupting line, so that the dressing is only partially applied over the skin surrounding the wound. Both sheets are then removed in toto while the margins of the thin film are smoothly conformed to the skin over the contours of the body.

The film 12 may be of any thin laminar material suitable for being placed in contact with skin surrounding a wound. A preferred body-conformable film is made from an elastomer of synthetic rubbery material, preferably an amorphous (when unstretched) synthetic polymer of relatively high molecular weight (mol wt%), preferably in the range from about 10,000 to about 1,000,000. Such a polymer rapidly returns to approximately its initial dimensions and shape after substantial deformation by a weak stress and release of the stress. More specifically, we refer to a polymer which retracts within 1 minute to less than 1.5 times its original length after being stretched at room temperature (20° C.) to twice its length and held for 1 min before release. Elastomers particularly useful in this invention are elastic at room temperature, that is, they are above their glass transition temperature ($T_g$). Films with substantial crystallinity are not elastomeric and are unsuited for use in our wound dressing.

The specific elastomer used will depend upon the particular type of wound for which the dressing is to be used, and the length of time the dressing may be expected to be kept on the wound before it is changed. Suitable elastomers include ethylene-co-vinyl acetate; ethylene-co-methylacrylate; butadiene-co-acrylonitrile; isobutylene-co-isoprene; terpolymer of ethylene, propylene and a diene sidechain; ethyl acrylate-co-butadiene; Estane* brand urethanes formed by the reaction of (a) diisocyanates and polyalkylene polyether glycols, or (b) diisocyanates and polyalkylene polyester glycols; Hycar* brand butadiene-acrylonitrile modified with carboxyl groups; Hydrin* brand copolymer of epichlorohydrin with ethylene oxide; styrene-butadiene-styrene block copolymers available under the Kraton brand; Hytrel brand copolyester, and the like, which are essentially liquid-impervious, do not absorb a significant amount of moisture, and can be formed into thin smooth surfaced sheets in the range from about 0.5 mil to about 1 mil thick.

In the best mode of the invention a thermoplastic Estane brand polyurethane formed by the reaction of long chain polyols having a mol wt of from about 400 to about 10,000, preferably 800 to 6000, with diisocyanates and chain extending agents (preferably short chain polyols) having a mol wt of up to about 400, and the NCO/OH ratio is generally in the region of from 0.95:1 to 1.1:1. Preferred films are transparent, that is light permeable, or translucent, as is the adhesive coating for the film. Adhesive coatings, preferably moisture-permeable adhesive coatings for use in adhesive film wound dressings and methods for spreading the adhesive continuously or discontinuously over the entire face of the film, or in a predetermined pattern thereupon, are well known in the art and are described in British Patent No. 819,635 and 1,280,631. Preferred adhesives are blends of high and low viscosity polyvinyl ethyl ethers; and, copolymers of an acrylate ester with acrylic acid, for example as disclosed in European Patent Application No. 35399. A specific adhesive comprises a copolymer, polymerized in acetone, of 47 parts by weight of butyl acrylate, 47 parts of 2-ethylhexyl acrylate and 6 parts of acrylic acid, the copolymer having an intrinsic viscosity of at least 1.9 dl/gm. The desirable coating of adhesive is at least as water-vapor permeable as the film.

It has been found that the interrupting line will only serve as a temporary stop if the peel strength is not too high, though its lower value is not narrowly critical. The upper limit is about 10 oz/inch of width (or about 100 gm/cm of width), the precise value varying depending upon the particular adhesive and release sheet stock used. The peel strength is measured by a method analogous to ASTM D-3330 for Peel Adhesion of Pressure-Sensitive Tape at 180°, using a Chatillon Model DPP-1 Kg push/pull (tension/compression) gauge attached to a 1" wide strip of release sheet adhered coextensively to a 1" wide strip of adhesive-coated film. One end of the film is held securely while the release sheet at that end is pulled linearly in the same plane but in a direction away from the held end, that is, at an angle of 180°. A preferred peel strength is in the range from about 0.5 oz/in to about 5 oz/in of width. There is no narrowly critical lower limit for the peel strength.

As already stated, each side-margin must be wide enough in relation to the area of the dressing to permit the film to be tensioned while it is being applied. In a very small dressing, say 2" wide ×3" long, the side-margins are typically each 0.75" wide, so that the combined area of the side-margins is 3 in$^2$, and the ratio of the area of the margins to that of the dressing is 50% which is the upper limit of the ratio. In a very large dressing, 7" width×9" long, each side margin is typically 1" wide, so that the ratio of the area of the margins to that of the dressing is 14/63 or 22%. Thus the ratio ranges from about 20% for large dressings to about 50% for small ones.

Moisture-permeable synthetic resinous films are disclosed in U.S. Pat. Nos. 3,645,835 and 4,657,006, British Patent Specification No. 1280631, in European Patent Application No. 51935, the disclosures of which patents are incorporated by reference thereto as if fully set forth herein. Preferred are adhesive-coated films having a water vapor transmission rate (WVTR) of at least 250 gm per square meter per 24 hr period when measured at 37° C. and 100% to 10% relative humidity difference by the Payne Cup method, more preferably greater than 400 gm/m$^2$/24 hr, with a film about 1 mil (25 microns) thick, coated with a layer of pressure-sensitive acrylic ester copolymer adhesive having a thickness of about 1 mil. The WVTR may be as high as about 3000 gm/m$^2$/24 hr but is typically no more than about 1000 gm/m$^2$/24 hr. The foregoing criteria for WVTR may be met with either continuous or microporous films having an average pore size less than 2 microns, preferably less than 0.1 micron.

Such long chain polyols include virtually all known polyesters, polylactones, polyethers, polythioethers, polyester amides, polycarbonates, polyacetals, and vinyl polymers which contain Zerewitinoff active groups (mainly hydroxyl groups), with the optional addition of minor quantities of compounds of this type containing three Zerewitinoff active groups. Examples of such polyols include: polybutadiene diols, polyhydroxyl compounds already containing urethane or urea groups, modified and unmodified natural polyols and compounds containing other Zerewitinoff active groups, such as amino, carboxyl or thio groups. These compounds are known in the art and have been described in U.S. Pat. Nos. 3,963,679; 3,984,607; 4,035,213; inter alia.

Preferred linear polyols are derived from hydroxyl containing polyesters of glycols or adipic acid, phthalic and/or terephthalic acid and the hydrogenation products thereof, hydroxyl polycaprolactones, polyethylene oxide, polypropylene oxide, polytetrahydrofuran; and, mixed polyethers of ethylene oxide and propylene oxide. The ether units in such polyurethanes may be said to be derived from ethylene diol and a propylene or butylene diol; that is, they will contain $CH_2CH_2O$—units and —$CH_2CH_2CH_2O$—, —$CH_2CH(CH_3)O$—or —$CH_2CH_2CH_2CH_2O$—units.

Suitable diisocyanates for use according to the present invention include aliphatic, cycloaliphatic, aromatic, araliphatic and heterocyclic diisocyanates which are known in the art. The following are preferred for the purposes of this invention: hexamethylene diisocyanate, optionally with methyl substituents, isophorone diisocyanate and 4,4'-di-phenylmethane diisocyanate (MDI). Most preferred are the reaction product of polytetramethylene ether glycol and MDI, usually chain extended with an alkane diol having a number average mol wt in the range from about 10,000 to about 70,000. The excellent conformability of the film is attributable to its 50% stretch modulus which approximates that of human skin.

Having thus provided a general discussion, and specific illustrations of the best mode of making and using the wound dressing described hereinabove, it is to be understood that no undue restrictions are to be imposed by reason thereof, except as provided by the following claims.

We claim:

1. An adhesive wound dressing comprising:
an elastomeric film having a biocompatible adhesive uniformly coated on at least a portion of the front surface thereof in an amount sufficient to secure said dressing to an injured body, said dressing having opposed first and second side-margins at first and second side-edges of said film; and,
first and second release sheets which together completely cover said adhesive, each unit area of said release sheets having the same numerically quantifiable attachment to said adhesive, said attachment being measured by the peel strength of each release sheet;
said first release sheet having a single fold therein which provides a fold-line in spaced-apart relation parallel to said first side-edge and extending the width of said first release sheet so as to define said first side-margin having a width wide enough in relation to the area of said dressing to permit said film to be tensioned, one folded portion of said first release sheet being adhesively attached at said first side-margin, the other folded portion providing a first gripping tab exteriorly folded upon and overlying the surface of said one folded portion;
said second release sheet lying substantially coextensively and planarly upon said front surface while releasably adhered thereto, one end of said second release sheet providing a second gripping tab overlying said first gripping tab, the remaining portion of said second release sheet being releasably adhered to said front surface;
said second release sheet having a single interrupting line of spaced apart incisions pierced therethrough, from the outer surface of said sheet to its inner surface in contact with said adhesive, said interrupting line being in spaced-apart relation to said second side-edge, and distally spaced apart from said fold-line, said interrupting line extending laterally over a major portion of the lateral dimension of said second side-margin;
whereby the act of pulling apart said gripping tabs facilely exposes said adhesive and allows said film to be deftly positionable aseptically upon said wound, and tensionable smoothly over the contours of the body, as a natural consequence of said act.

2. The wound dressing of claim 1 wherein said film is moisture-permeable having a water vapor transmission rate of at least 300 gm/m$^2$/24 hr, measured at 37° C. across a relative humidity difference of 100% to 10%.

3. The wound dressing of claim 2 wherein said film is continuous, or microporous having pores less than 2 microns in average diameter.

4. The wound dressing of claim 3 wherein said film is a polyurethane derived from linear polyols in turn derived from hydroxyl-containing polyesters of glycols or adipic acid, phthalic and/or phthalic acid and the hydrogenation products thereof, hydroxyl polycaprolactones, polyethylene oxide, polypropylene oxide, polytetrahydrofuran, and, mixed polyethers of ethylene oxide and propylene oxide; and, a diisocyanate; optionally chain extended with a short chain polyol.

5. The wound dressing of claim 3 wherein said film is less than about 2 mils thick, and said adhesive is selected from the group consisting of a blend of high and low viscosity polyvinyl ethyl ethers, and, copolymers of an acrylate ester with acrylic acid, the adhesive being spread as a coating having a thickness less than about 2 mils.

6. The wound dressing of claim 3 wherein said interrupting line is formed with a multiplicity of closely spaced apart slits or perforations having an average open area of less than about 20 mm$^2$ linearly spaced apart less than about 5 mm, one from the other.

7. The wound dressing of claim 3 wherein said said second release sheet is larger in area than the first, said first margin being sufficiently wide to permit it and said first gripping tab to be gripped between the the thumb, index and middle fingers at the same time; each said margin being wide enough in relation to the area of said dressing to permit said film to be tensioned.

8. The wound dressing of claim 3 wherein said release sheets are cut from the same stock of flexible silicone-coated sheet and said side first and second side-margins are at least 1.25 cm wide (0.5 inch).

9. The wound dressing of claim 3 wherein said fold-line and said interrupting line are equidistant from the lateral center line of said dressing.

10. The wound dressing of claim 3 wherein said adhesive uniformly coated on said front surface is permeable to water vapor.

11. The wound dressing of claim 7 including a pad of absorbent gas-permeable fabric formed of fibers held in place by interlocking and frictional engagement with each other, said pad being adhesively secured to said elastomeric film intermediate said side-margins.

12. The wound dressing of claim 8 wherein said fabric of fibers includes a layer of flexible hydrophilic absorbent polymeric material which is deposited substantially in the fabric.

13. An adhesive wound dressing comprising,
an elastomeric film having a biocompatible adhesive uniformly coated on at least a portion of the front surface thereof in an amount sufficient to secure said dressing to an injured body, said dressing having opposed first and second side-margins at first and second side edges of said film; and,
first and second release sheets which together completely cover said adhesive, each unit area of said release sheets having the same numerically quantifiable attachment to said adhesive, said attachment being measured by the peel strength of each release sheet;
said first release sheet having (i) a single first interrupting line of spaced-apart incisions pierced therethrough, from the outer surface of said first release sheet to its inner surface in contact with said adhesive, said first interrupting line being parallel to and in spaced-apart relation to said first side-edge to define said first side-margin having a width wide enough in relation to the area of said dressing to permit said film to be tensioned, to which margin one end of said first release sheet is releasably adhered, said first interrupting line extending over a major portion of the length of said first side-margin, and (ii) a first gripping tab provided by the other end of said first sheet being folded upon itself, exteriorly;

said second release sheet lying coextensively and planarly upon said front surface while releasably adhered thereto, one end of said second release sheet providing a second gripping tab overlying said first gripping tab, the remaining portion of said second release sheet being releasably adhered to said front surface;

said second release sheet having a single second interrupting line of spaced apart incisions pierced therethrough, from the outer surface of said sheet to its inner surface in contact with said adhesive, said second interrupting line being parallel to and in spaced-apart relation to said second side-edge to define said second side-margin having a width wide enough in relation to the area of said dressing to permit said film to be tensioned, and distally spaced apart from said first gripping tab, said second interrupting line extending over a major portion of the length of said second side-margin of said film; whereby the act of pulling apart said gripping tabs facilely exposes said adhesive and allows said film to be deftly positionable, aseptically upon said wound, and tensionable smoothly over the contours of the body, as a natural consequence of said act.

14. The wound dressing of claim 13 wherein said film is moisture-permeable having a water vapor transmission rate of at least 300 gm/m$^2$/24 hr, measured at 37° C. across a relative humidity difference of 100% to 10%.

15. The wound dressing of claim 14 wherein said film is continuous, or microporous having pores less than 2 microns in average diameter.

16. The wound dressing of claim 15 wherein said film is a polyurethane derived from linear polyols in turn derived from hydroxyl-containing polyesters of glycols or adipic acid, phthalic and/or phthalic acid and the hydrogenation products thereof, hydroxyl polycaprolactones, polyethylene oxide, polypropylene oxide, polytetrahydrofuran, and, mixed polyethers of ethylene oxide and propylene oxide; and, a diisocyanate; optionally chain extended with a short chain polyol.

17. The wound dressing of claim 15 wherein said film is less than about 2 mils thick, and said adhesive is selected from the group consisting of a blend of high and low viscosity polyvinyl ethyl ethers, and, copolymers of an acrylate ester with acrylic acid, the adhesive being spread as a coating having a thickness less than about 2 mils.

18. The wound dressing of claim 15 wherein said interrupting line is formed with a multiplicity of closely spaced apart slits or perforations having an average open area of less than about 20 mm$^2$ linearly spaced apart less than about 5 mm, one from the other.

19. The wound dressing of claim 15 wherein said adhesive coated uniformly on said front surface is permeable to water vapor and the ratio of the combined area of said side-margins is in the range from about 20% to about 50% of the area of said film.

20. The wound dressing of claim 15 wherein said first and second release sheets are each adhesively secured to said adhesive with essentially the same peel strength in the range from 0.5 oz/in of width to about 5 oz/in of width.

21. The wound dressing of claim 15 wherein the ratio of the combined area of said side-margins is in the range from about 20% to about 50% of the area of said film.

22. The wound dressing of claim 15 wherein said second release sheet covers essentially the same area of said front surface as the first, and each said margin is at least 1.25 cm (0.5 inch) in width.

23. The wound dressing of claim 19 wherein said first and second interrupting lines are equidistant from the lateral center line of said dressing.

24. The wound dressing of claim 19 wherein said release sheets are cut from the same stock of flexible silicone-coated sheet, and said side-margins are about 1" wide.

25. The wound dressing of claim 23 including a pad of absorbent gas-permeable fabric formed of fibers held in place by interlocking and frictional engagement with each other, said pad being adhesively secured to said elastomeric film and substantially centered intermediate said side-margins.

26. The wound dressing of claim 25 wherein said first and second interrupting lines are equidistant from the lateral center line of said dressing.

27. The wound dressing of claim 25 wherein said fabric of fibers includes a layer of flexible hydrophilic absorbent polymeric material which is deposited substantially in the fabric.

* * * * *